United States Patent [19]
Murphy et al.

[11] Patent Number: 6,057,693
[45] Date of Patent: *May 2, 2000

[54] DIELECTRIC MIXTURE COMPOSITION SENSOR WITH COMPENSATION FOR MIXTURE ELECTRICAL CONDUCTIVITY

[75] Inventors: J. Brian Murphy, Culver City; John M. Brauninger, Los Angeles; John McHardy, Westlake Village; Clifford A. Megerle, Thousand Oaks; Carl W. Townsend, Los Angeles, all of Calif.

[73] Assignee: Raytheon Company, Lexington, Mass.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/703,498

[22] Filed: Aug. 27, 1996

[51] Int. Cl.$^7$ ............................ G01N 27/22; G01N 33/22
[52] U.S. Cl. ........................ 324/663; 324/444; 324/672; 324/688; 73/61.43
[58] Field of Search ........................ 324/444, 654, 324/663, 672, 688; 73/61.41, 61.43, 61.44

[56] References Cited

U.S. PATENT DOCUMENTS

| | | | |
|---|---|---|---|
| 5,134,381 | 7/1992 | Schmitz | 324/685 |
| 5,343,156 | 8/1994 | Johnson | 324/672 |
| 5,345,183 | 9/1994 | Take | 324/663 |
| 5,589,778 | 12/1996 | Ono | 324/654 |

*Primary Examiner*—Glenn W. Brown
*Attorney, Agent, or Firm*—Colin M. Raufer; Leonard A. Alkov; Glenn H. Lenzen, Jr.

[57] ABSTRACT

The composition of an electrically conductive mixture, such as a mixture of gasoline and alcohol, is measured using a single measurement cell having a first electrode and a second electrode with a measurement space therebetween for receiving a specimen of the mixture. With a specimen of the mixture in the measurement space, the first electrode is alternatively connected to a reference discharge voltage, preferably ground, and to an applied voltage through a resistor. A first operational state encompasses the period when the first electrode is connected to the reference discharge voltage and a second operational state encompasses the period when the first electrode is connected to the applied voltage through the resistor. A first operational state peak voltage is measured during the first operational state, and a second operational state peak voltage is measured during the second operational state. The first operational state peak voltage and a preselected constant proper fraction of the second operational state peak voltage are summed to obtain a summed voltage output, which may be correlated to the composition of the mixture.

20 Claims, 5 Drawing Sheets

DIELECTRIC MIXTURE COMPOSITION SENSOR WITH COMPENSATION FOR MIXTURE ELECTRICAL CONDUCTIVITY

BACKGROUND OF THE INVENTION

This invention relates to the determination of the composition of electrically conductive mixtures, and, more particularly, to the determination of the composition of a gasoline-alcohol mixture using a compensated dielectric measurement.

It is sometimes necessary to determine the composition of a mixture which is electrically conductive because one or more of the components of the mixture are electrically conductive. One of the most important of such situations is the determination of the composition of a gasoline-alcohol mixture used as the fuel in the internal combustion engine of an automotive vehicle. In some areas, alcohol is added to gasoline for economic and environmental reasons. It is necessary to vary the control settings of the engine that uses such a fuel responsive to the alcohol content and composition of the mixture, in order to ensure its clean, efficient operation.

To control the engine settings responsive to the composition of the fuel, it is first necessary to measure the composition of the fuel in a reliable fashion. Techniques and apparatus for making such measurements of automotive fuels in real time are known. U.S. Pat. Nos. 5,231,258, 5,103,184, and 5,089,703 disclose a fuel sensor that makes such measurements capacitively. This approach is operable and reasonably accurate in many situations.

However, a potential inaccuracy in the composition measurements arises because the fuel may contain impurities such as salts that cause variations in its electrical conductivity even at constant composition and temperature. The dielectric properties of the fuel, upon which the capacitance measurements are based, vary somewhat according to its electrical conductivity. In particular, the actual composition of a highly conductive gasoline-alcohol fuel mixture may be somewhat different from that reported from readings of the capacitive sensor, because of such electrical conductivity effects.

In one approach to overcoming this problem, two sensors are provided, one to measure the capacitance of the fuel and the other to measure the electrical conductivity of the fuel. This approach is expensive in that two separate sensors are required, and may lead to instrumentation-based inaccuracies due to changes in characteristics of the two sensors over time.

There is a need for an improved approach to measuring the composition of a mixture such as a gasoline-alcohol mixture, which is both inexpensive to perform and accurate. The present invention fulfills this need, and further provides related advantages.

SUMMARY OF THE INVENTION

The present invention provides an apparatus and method for determining the composition of an electrically conductive mixture such as a gasoline-alcohol mixture. A more accurate determination of mixture composition is obtained than previously possible, with little added cost. The approach is based upon a capacitive measurement of the type already known in the art, but where the result of the capacitive measurement is corrected for variations in the electrical conductivity of the mixture. A single measurement cell of the type already known is used, and additional measurement capability is provided for more completely utilizing the data obtained during the capacitive measurement. Only minimal additional cost to obtain important additional accuracy is required.

In accordance with the invention, an apparatus for measuring the composition of an electrically conductive mixture comprises a measurement cell including a first electrode and a second electrode with a measurement space therebetween for receiving a specimen of an electrically conductive mixture. The second electrode is connected to a fixed second electrode potential, preferably ground. A voltage source has as an output an applied voltage, preferably a positive voltage relative to the grounded second electrode. A voltage oscillator switch is in electrical communication with the first electrode. The voltage oscillator is operable to alternatively connect the first electrode to a reference discharge voltage, preferably ground, and to the applied voltage through a resistor. A first operational state encompasses the period when the first electrode is connected to the reference discharge voltage, and a second operational state encompasses the period when the first electrode is connected to the applied voltage. A first measurement circuit element has an input in electrical communication with the first electrode and an output of a first operational state peak voltage measured during the first operational state. A second measurement circuit element has an input in electrical communication with the first electrode and an output of a second operational state peak voltage measured during the second operational state.

A mathematical circuit element has as inputs the first operational state peak voltage and the second operational state peak voltage, and as an output a mathematical function of the two peak voltages. Preferably, the output of the mathematical circuit element is the sum of the first operational state voltage and a preselected constant proper fraction of the second operational state peak voltage. The constant fraction is from about 0.1 to about 0.2 in the currently preferred embodiments, and is most preferably about 0.15. A correlator may be used to associate the summed voltage with the composition of the mixture, or the summed voltage may be used directly to control the engine operation.

In a related aspect, a method for measuring the composition of an electrically conductive mixture comprises the steps of providing a measurement cell including a first electrode and a second electrode with a measurement space therebetween for receiving a specimen of a mixture. The second electrode is connected to a fixed second electrode potential, preferably ground. A specimen of an electrically conductive mixture, preferably a gasoline-alcohol mixture, is placed into the measurement space. The first electrode is alternatively connected to ground and to an applied voltage through a resistor. A first operational state encompasses the period when the first electrode is connected to ground, and a second operational state encompasses the period when the first electrode is connected to the applied voltage through the resistor. A first operational state peak voltage is measured during the first operational state, and a second operational state peak voltage is measured during the second operational state. The two operational state peak voltages are mathematically combined as a voltage output. Preferably, the first operational state peak voltage and a preselected constant proper fraction of the second operational state peak voltage are summed to obtain a summed voltage output. The summed voltage output is preferably correlated with the composition of the mixture.

The peak voltage obtained during the first operational state, typically a negative peak voltage, reflects a capacitive measurement of the mixture, and specifically its dielectric constant upon which the first operational state peak voltage depends. This value, however, depends upon the electrical conductivity of the mixture, and may be slightly erroneous (as an indicator of mixture composition) when the mixture has a high electrical conductivity. The peak voltage obtained during the second operational state, typically a positive peak voltage, reflects an electrical conductivity (or alternatively stated, resistivity) measurement of the mixture. This second operational state peak voltage is of opposite sign from that of the first operational state peak voltage. Adding together the first operational state peak voltage and a fixed proper fraction of the second operational state peak voltage yields a summed voltage output that has been found to correlate closely with the actual mixture composition over a wide range of mixture electrical conductivities and mixture gasoline-to alcohol mixtures, and in particular for high mixture electrical conductivities where inaccuracies arose in prior measurements.

The improved accuracy is obtained without the need for a second sensor, and with only measurement modifications to a well-proved capacitive measurement sensor. The additional cost to obtain significant additional accuracy is therefore minimal. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
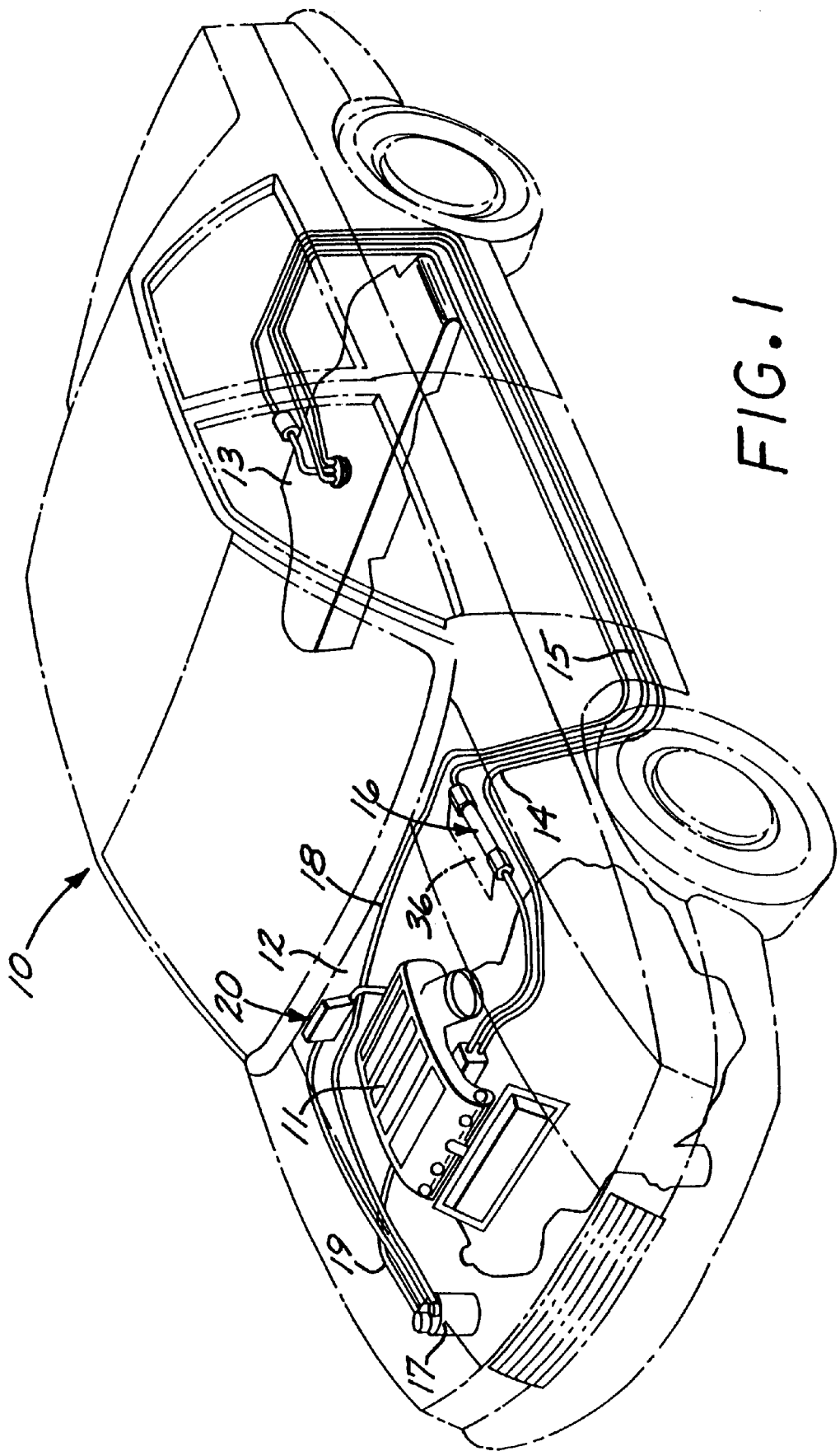
FIG. 1 is a perspective cutaway view of a motor vehicle having an engine fuel control with a fuel composition sensor according to the present invention.

FIG. 1 depicts a motor vehicle 10 with an internal combustion engine 11 in an engine compartment 12. The engine 11 receives fuel from a fuel tank 13 at the opposite end of the vehicle through a fuel conduit 15 and returns excess fuel to the tank 13 through a fuel conduit 14. The fuel in tank 13 may be a mixture of two fuels, one of which is gasoline and the other of which is an alcohol such as methanol or ethanol. The fuel may additionally include small impurity amounts of salts and water, or other electrically conductive compounds. The relative amounts of the major components, gasoline and alcohol, and the amount, if any, of any impurities present, such as salts and water, are not known a priori.

The engine is controlled responsive to the relative amounts of the gasoline and the alcohol present. To obtain information as to the relative amounts of gasoline and alcohol present in the fuel, the fuel conduit 15 includes therein a fuel composition sensor 16 located within the engine compartment 12 at a point close to the engine 11. The fuel composition sensor 16 generates an output signal indicative of the relative fractions of gasoline and alcohol in the fuel flowing therethrough.

A standard fuel vapor collection canister 17 is connected by a vapor conduit 18 to the fuel tank 13 for collection of vapor therefrom. Another vapor conduit 19 extends from the canister 17 to the induction system of the engine 11 to deliver the collected vapor to the engine 11 for combustion.

The operation of the engine 11 is controlled by an electronic controller 20, which may be located at the rear of the engine compartment as shown or at any other convenient location. The controller 20 may be a programmed digital computer similar to those presently used in motor vehicles for engine control. The apparatus is well known, comprising a microprocessor, RAM, ROM, and appropriate input/output circuitry, with an appropriate program stored in ROM to coordinate receipt of input information from various sensors, including the sensor 16, perform calculations and table look-ups, and output commands to various actuators of engine-related components. The controller 20 is responsive to the fuel composition output signal from the fuel composition sensor 16 as well as to a fuel temperature signal therefrom to modify such engine operating parameters as the air/fuel ratio, ignition timing, canister purge rate, and/or other parameters as necessary to optimize engine operation for the actual fuel mixture provided to the engine as sensed by the sensor 16.

Figure 2:
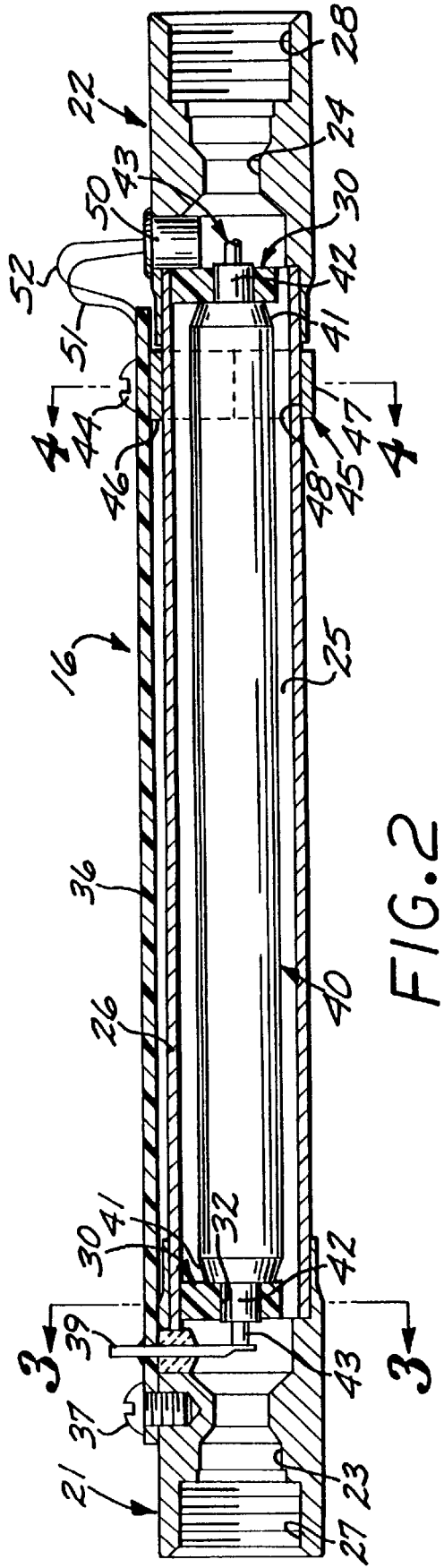
FIG. 2 is a side sectional view of a preferred fuel sensor.
Figure 4:
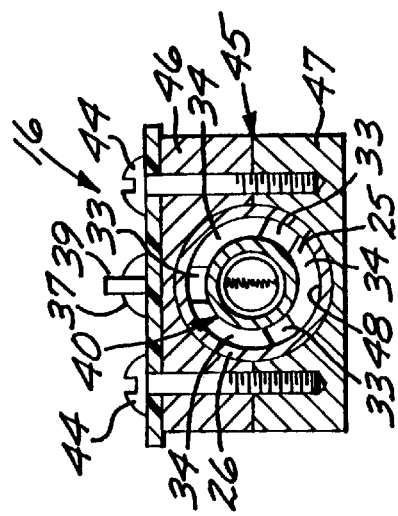
FIG. 4 is a sectional view of the fuel sensor of FIG. 2, taken generally along lines 4—4.
Figure 3:
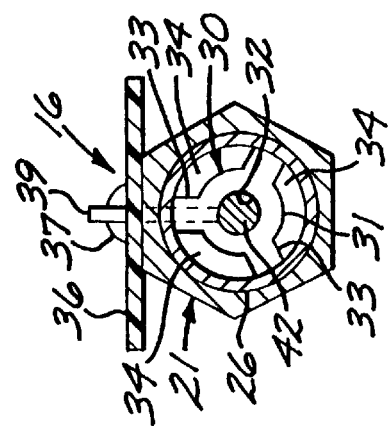
FIG. 3 is a sectional view of the fuel sensor of FIG. 2, taken generally along lines 3—3.

The mechanical structure of a preferred version of the sensor 16 is illustrated in FIGS. 2–4 and is also described in U.S. Pat. No. 5,103,184, whose disclosure is incorporated by reference. This structure provides for a common ground between the sensor case and the outer capacitor electrode, so that it is not necessary for these parts to be insulated from each other, although an insulated approach without a common ground is also operable.

An outer tube 26 of low carbon stainless steel has a first end fitted within and laser welded to an extended open end of a coupling member 21 and a second end fitted within an laser welded to an extended open end of another coupling member 22. The coupling members 21 and 22 are both made of stainless steel, have an outer hexagonal shape, and define passages 23 and 24, respectively, therethrough. Each of the passages 23 and 24 is provided with an internally threaded portion 27 and 28, respectively, for attachment with an appropriate fitting to the fuel line 15. The outer tube 26 forms a portion of the outer case of the sensor 16 as well as the outer electrode of a sensor capacitor.

A stainless steel inner tube 40 is disposed axially within the outer tube 26 to form the inner electrode of the sensor capacitor and to define an annular chamber 25 between the tubes 26 and 40. The inner tube 40 is closed at each end in a tapered portion 41, a smaller diameter cylindrical portion 42, and an extended axial nipple 43, all made of stainless steel. The inner tube 40 is suspended at each end thereof within the outer tube 40 by spacers 30, seen axially in FIG. 3. Each spacer 30 includes an inner portion 31 having a circular opening 32 which receives the cylindrical portion 42 of the inner tube 40 and three radially projecting legs 33 at 120 degree angles with respect to each other, which end at the outer tube 26. The legs 33 define openings 34 therebetween. The spacers 30 may be made of an alcohol resistant, electrically insulating polymeric resin such as Nylon®. A fuel flow path is thus defined through passage 24 of coupling member 22, through the openings 34 between the legs 33 of the first spacer 30, through the annular chamber 25 between the tubes 26 and 40, through the openings 34 between the legs 33 of the second spacer 30 at the other end of the tube, and through the passage 23 of the coupling member 21. The fuel in the chamber 25 between tubes 26 and 40 forms the dielectric of the sensor capacitor defined by the tubes 26 and 40, which serve as the electrodes.

A circuit board 36 of standard construction is mounted as part of the sensor 16 and supports the electronic circuitry discussed subsequently. The circuit board 36 is attached to the coupling member 21 by a machine screw 37. The machine screw 37 not only physically anchors one end of the board 36 but also provides an electrical ground connection between a ground circuit trace on the circuit board 36 and, through coupling member 21, the tube 26. The tube 26 thus comprises a grounded electrode of the sensor capacitor. Between screw 37 and the adjacent spacer 30, a glass insulator 38 is retained in an opening of the coupling member 21 adjacent to the circuit board 36. A stainless steel pin 39 projects through the circuit board 36 and the insulator 38 so that it does not contact the coupling member 21 or the tube 26. The pin 39 is maintained in physical and electrical contact, as by welding or soldering, to the adjacent nipple 43 and is soldered on circuit board 36 to the appropriate trace for the inner electrode of the sensor capacitor. The inner and outer electrodes are thus electrically coupled to the appropriate elements on the circuit board.

The opposite end of the circuit board 36 is attached by a pair of screws 44 to a clamp 45 comprising upper and lower clamp members 46 and 47, respectively. The screws 44 hold the clamp members 46 and 47 together as well as securing the clamp 45 to the circuit board 36. The clamp members 46 and 47 include matching semicircular openings which, together, define an inner circular opening 48 for receiving the outer tube 26. The clamp 45 fits snugly around the tube 26 to hold the opposite end of the circuit board 36 in a stable manner without undue vibration relative to the tube 26 but which allows relative rotation so that twisting torques applied between coupling members 21 and 22 are not applied to the circuit board 36. In practice, to protect the components of the circuit board 36 and other parts of the sensor 16 from the environment, a supplemental external case, not shown, may be attached to the sensor 16 as by a machine screw in a threaded depression, not shown, opposite the screw 37 and at clamp 45, for example by extending the bolts 44 completely therethrough to surround all of the sensor except the hexagonal ends of the couplings 21 and 22.

A fuel temperature sensor 50 is received in a sealing manner in the wall of the coupling member 22 so as to be exposed to fuel within. The sensor 50 generates a fuel temperature signal communicated to an appropriate circuit trace on the circuit board 36 through wire leads 51 and 52. The fuel temperature sensor may be a thermistor or any other type of temperature sensor appropriate for sensing the temperature of fluids and provides a temperature correction signal for the sensor output. The fuel temperature signal may be separately output to the engine control computer 20 for temperature compensation of the fuel composition signal received from the sensor 16.

Although all openings and gaps within the sensor 16 are of sufficient size to prevent them from presenting a significant restriction to fuel flow, the total volume of fuel contained within the chamber 25 is minimized to prevent extreme reduction or accumulation of fuel within the chamber 25 which might lead to differences in dielectric constant between the fuel mixture in the sensor and that about to enter the combustion chamber of the engine 11.

Figure 5:
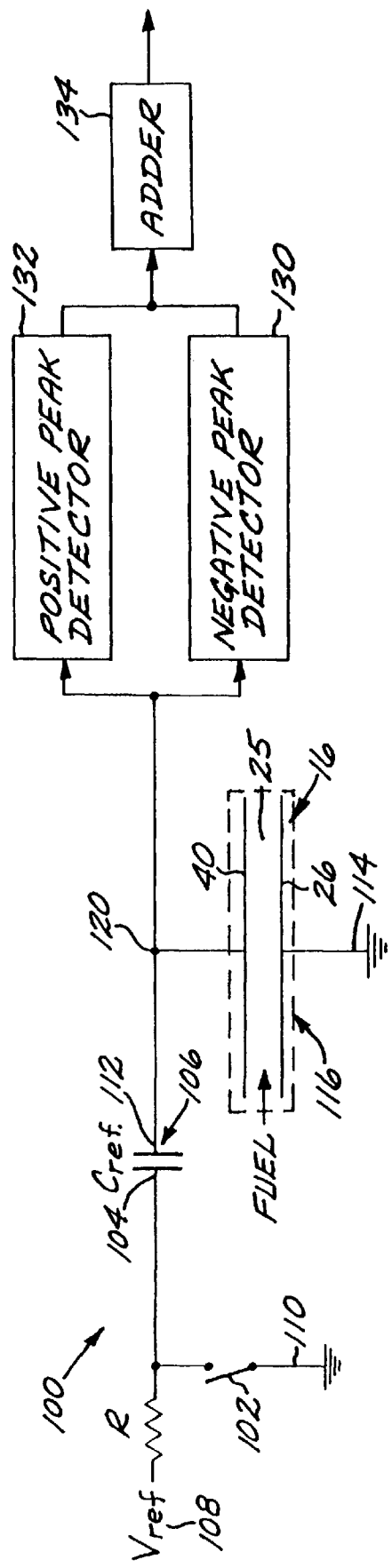
FIG. 5 is a schematic view of the electronics circuitry of the sensor.

FIG. 5 schematically depicts a sensor electronics circuit 100 in relation to the fuel sensor 16. The components of the circuit 100 are preferably mounted on the circuit board 36 and connected to the interior components of the sensor 16 in the manner previously described. The components may be provided as discrete components or as an integrated circuit for mass production.

In the circuit 100, an oscillating voltage switch 102 alternatingly connects a first side 104 of a reference capacitor 106, $C_{ref}$, to a voltage 108, $V_{ref}$, through resistor R, or to ground 110. A second side 112 of the reference capacitor 106 is connected to ground 114 through a variable capacitor 116 formed by the tubes 26, and the fuel in the chamber 25 of the sensor 16. As illustrated, the inner tube 40 is connected to the second side 112 of the reference capacitor 106. The outer tube 26 is connected to ground 114. The fuel to be sensed flows in the chamber 25 defined between the tubes 26 and 40 and forms the dielectric medium of the variable capacitor 116.

Figure 6:
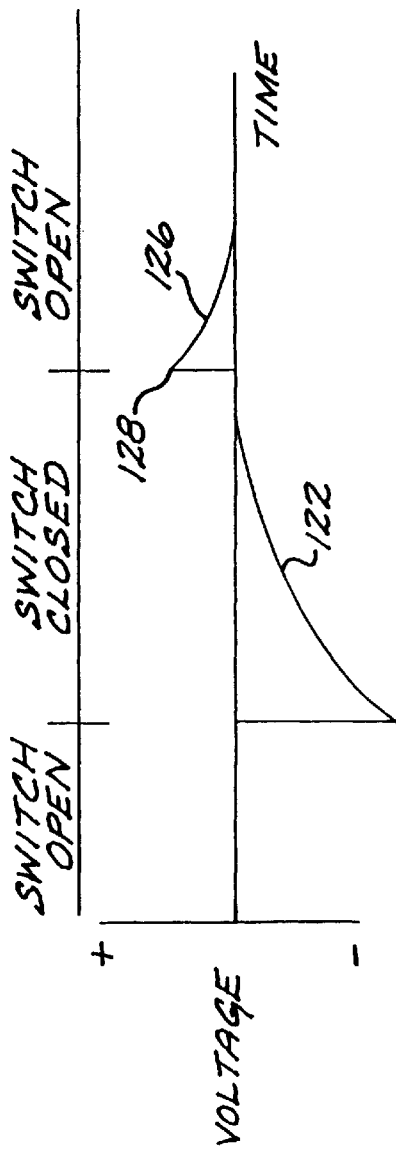
FIG. 6 is a graph of voltage as a function of time at the measurement point of the electronics circuitry.

The present approach measures voltage responses at a measurement point 120 at the second side 112 of the capacitor 106, or equivalently, the inner tube 40. Starting from an initial condition with the switch 102 open, when the switch 102 is closed after the reference capacitor 106 has been previously charged, the reference capacitor 106 discharges to ground 110 and a transient negative voltage spike 122 having a maximum (negative) peak value 124 is observed at the measurement point 120, as seen in FIG. 6. (The transient voltages discussed herein presuppose that $V_{ref}$ is positive relative to ground, the preferred case. They are reversed if $V_{ref}$ is negative.) When the switch 102 is later opened, the reference capacitor 106 charges from the reference voltage 108. A transient positive voltage spike 126 with a maximum (positive) peak value 128 is observed.

These same transient voltages were observed and reported at col. 7, lines 29–39 of the '184 patent, see also FIG. 7(C) of the '184 patent. The '184 patent makes use of the information in the negative voltage spike 122, but expressly states that it does not use the information in the positive voltage spike 126.

The present inventors have discovered that the information in the positive voltage spike 126 may be used to correct the output information for the conductivity variations in the fuel. Accordingly, the circuit 100 is provided with a first measurement circuit in the form of a negative peak detector 130 to detect the negative peak value 124 ($V_{peak-}$), and a second measurement circuit in the form of a positive peak detector 132 to detect the positive peak value 128 ($V_{peak+}$). The negative peak detector 130 is preferably a comparator/pulse integrator feedback circuit, and the positive peak detector 132 is preferably an operational amplifier/comparator circuit.

The outputs of the peak detectors 130 and 132 are provided to a mathematical circuit element, which in the preferred embodiment is an adder 134. The adder 134 adds mathematical functions of the negative peak value 124 and the positive peak value 128 together. The output signal of the adder 134 is provided to the engine controller 20 as the output signal of the sensor 16. More generally, the negative peak value 124 and the positive peak value 128 may be combined in a nonlinear fashion by a different circuit element substituted for the adder 134. The inventors have found that a linear combination yields a good correlation with the test data, but in other circumstances nonlinear combinations of the inputs may be required to correlate the test data.

For the sensor geometry of FIGS. 2–4, the preferred mathematical function of the negative peak value $V_{peak-}$ is the negative peak value itself. The preferred mathematical function of the positive peak value $V_{peak+}$ is a preselected constant proper fraction of the positive peak value. The constant proper fraction ranges from about 0.1 to about 0.2 for the preferred sensor and circuitry. Correlations have demonstrated that selection of a proper fraction of 0.15 reduces errors caused by conductive components in the fuel to about one percent over a wide range of fuel composition (fractions of gasoline and alcohol, for both ethyl and methyl alcohols) and conductive impurity contents. Thus, the preferred output of the adder 134 for the sensor of FIGS. 2–4 is $(V_{peak-} + 0.15\ V_{peak+})$.

As discussed in the '184 patent, the value of $V_{peak-}$ gives an indication and measurement of the dielectric constant of the fuel in the chamber 25. However, studies by the present inventors have determined that the dielectric constant value determined from $V_{peak-}$ is also weakly a function of the fuel electrical conductivity (or equivalently, resistivity). Consequently, there may be an error in the determination of the fuel composition if only the value of $V_{peak-}$ is used to establish the output signal of the sensor 16, as has been the prior practice.

The studies by the inventors have further determined that the value of $V_{peak+}$ is a function of the fuel conductivity and, also, a weak function of the dielectric constant. The mathematical combination of the values of $V_{peak-}$ and $V_{peak+}$ may therefore be used, as described herein, to compensate for the effect of the dependence of $V_{peak-}$ on the fuel conductivity.

The components of the circuit 100 may be any operable circuit elements. However, an important consideration in the competitive world of automotive manufacture is obtaining satisfactory performance with minimal cost of components and production. The considerations of satisfactory performance and cost together determined the selection of the preferred circuit components for the present application.

Figure 7:
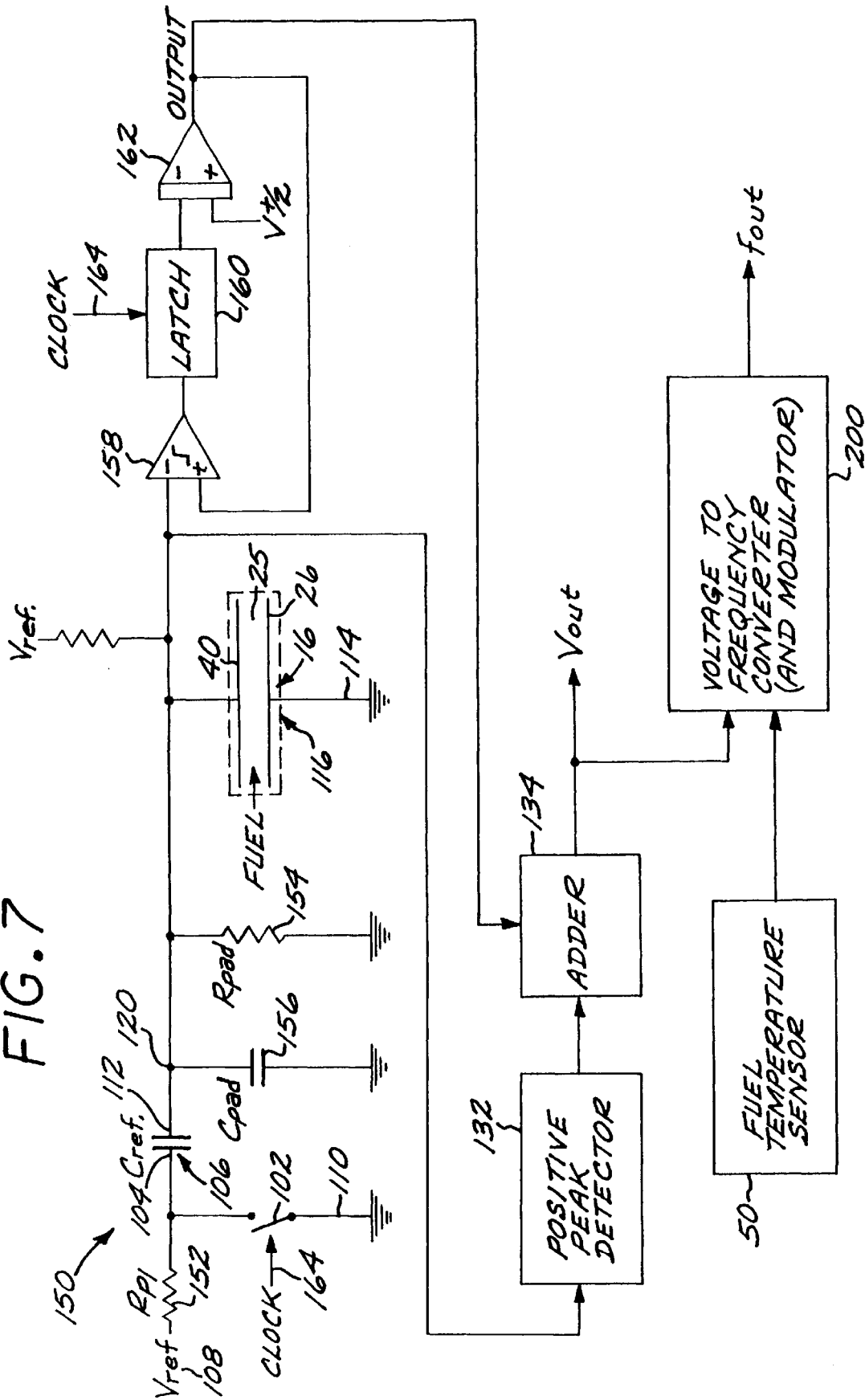
FIG. 7 is a schematic view of a preferred implementation of the electronics circuitry of the sensor.

FIG. 7 depicts a preferred form of a measurement circuit for practical applications with minimal cost. In FIG. 7, elements corresponding to those of the embodiment of FIG. 5 are assigned the same reference numerals, and the earlier description is incorporated here.

In the measurement circuit of FIG. 7, resistor 152, $R_{pl}$, is added in series with the reference voltage 108, to limit the current that may be drawn. A resistor 154, $R_{pad}$, and a capacitor 156, $C_{pad}$, are added in parallel with the fuel sensor 16 to minimize the range of nonlinear variation.

The negative peak detector 130 is implemented as a high-speed comparator 158, preferably an LT 1016 comparator, and a latch 160 that sequentially determine the values of $V_{peak-}$ and supply the values to an integrator 162. The latch 160 is provided a clock input 164 that corresponds to a clock input 164' that times the switch 102, so as to capture the value of $V_{peak-}$ properly.

The positive peak detector 132 may be either an open-loop type, with a diode or emitter-follower, or a closed loop type. The open-loop types have low cost and good speed, but relatively low precision. The open-loop types have good precision, but higher cost. An LT1016 comparator of the type discussed in the '184 patent and used for the negative peak detector is operable, but of relatively high cost.

Figure 8:
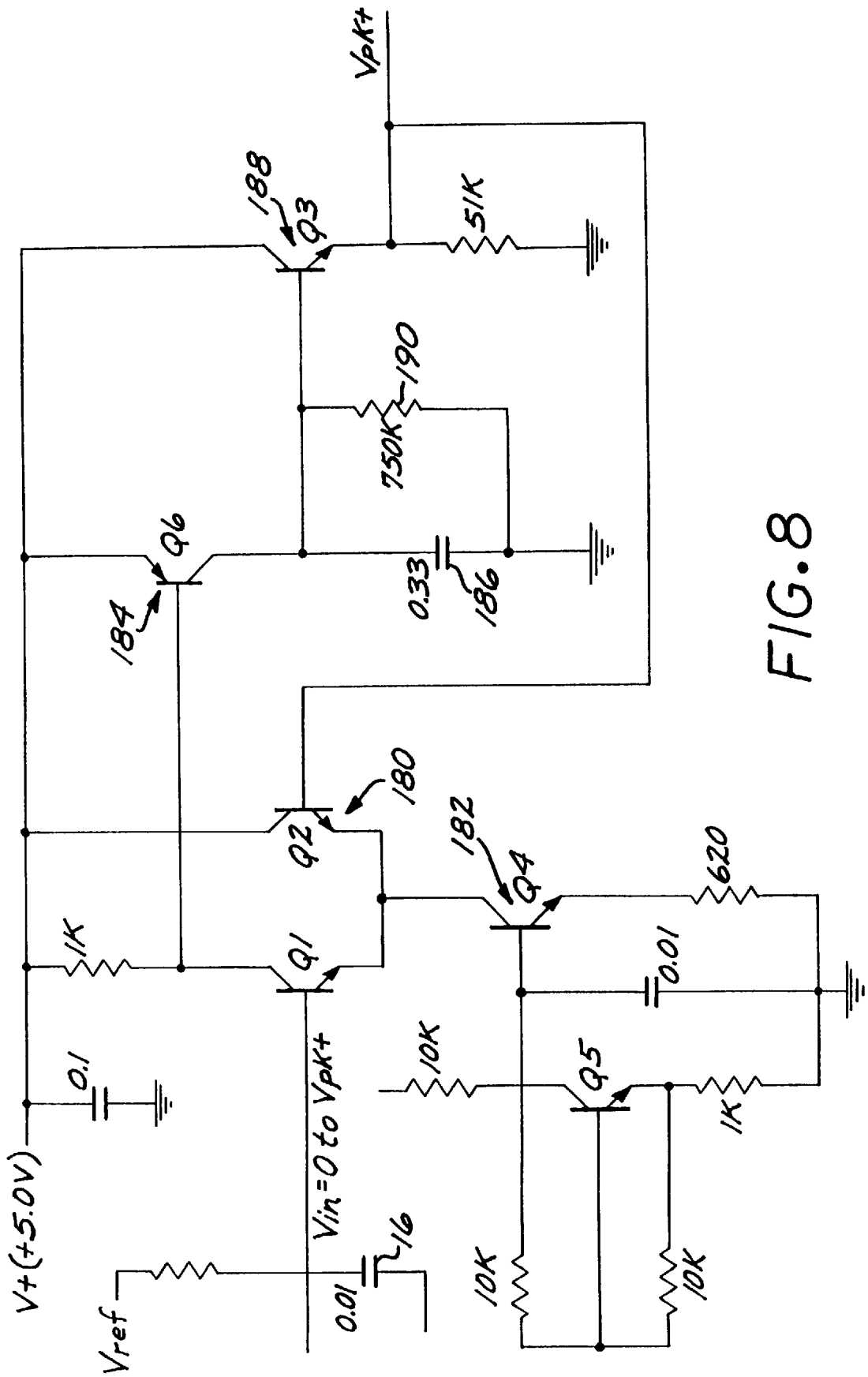
FIG. 8 is a electronic schematic diagram of a preferred positive peak detector.

The preferred positive peak detector 132 is illustrated in greater detail in FIG. 8. An input voltage from the fuel sensor 16 is provided to a differential amplifier 180, which receives a current input from a temperature-compensated current source 182. If the positive peak voltage is less than the input voltage, the differential amplifier 180 turns on transistor 184. Capacitor 186 then charges rapidly until the output voltage equals the input voltage. Transistor Q2 of the differential amplifier 180 is thence turned on, transistor Q1 is turned off, and transistor 184 is turned off so that the output and input voltages are the same. The peak voltage value is followed by the emitter follower buffer 188. As the input voltage drops as shown in FIG. 6, the output voltage $V_{peak+}$ is maintained due to the discharge of the capacitor 186 through a resistor 190 over a relatively long period of time. This positive peak detector is relatively inexpensive and is operable to capture the peak voltage which has a rise time in the 1–10 microsecond range. This relatively slow response is actually desirable, as it ignores transients on the signal. The accuracy of this circuit is not particularly great, but it is sufficient in view of the relatively weak dependence of the result on the value of $V_{peak+}$.

The peak values determined by the negative peak detector 130 and the positive peak detector 132 are supplied to the adder 134, as discussed previously. The output of the adder 134 is the $V_{out}$ signal. The output of the adder 134, $V_{out}$, is supplied to the engine controller For some applications, it may be desirable to provide a frequency output rather than a voltage output. For such situations, the voltage output $V_{out}$ of the adder 134 is supplied to a voltage-to-frequency converter 200, resulting in a signal $f_{out}$ whose frequency is proportional to $V_{out}$. Optionally, temperature information from the fuel temperature sensor 50 may be encoded as an amplitude modulation onto the frequency signal $f_{out}$ by the voltage-to-frequency converter 200.

The $V_{out}$ or $f_{out}$ signals may be used directly for control functions, or they may optionally be correlated with prior test data to obtain the actual values of the composition of the mixture. Correlation is preferably accomplished using a look-up table in the electronic controller 20.

The circuit of FIG. 7 may be selected to have a set of most-preferred components and values, as discussed next. The fuel sensor 16 is preferably the cylindrical geometry of FIGS. 2–4, with the outer radius of the inner tube 40 being 0.2275 inches and the inner radius of the outer tube 26 being 0.2275. The voltage $V_{ref}$ is +3.5 volts DC. The switch 102 is preferably a 2N7000 MOSFET driven at a switching speed of about 5–10 KHz. The value of $R_{pl}$, is chosen as a compromise between increasing the value of $R_{pl}$ to decrease the dependence of $V_{peak+}$ on the capacitance and decreasing the value of $R_{pl}$, which increases the value of $V_{peak+}$, making it easier to measure. For the preferred case, $R_{pl}$, was chosen as 5,000 ohms. $C_{pad}$ was chosen as 330 pf, and $R_{pad}$ was chosen as 2000 ohms.

A fuel sensor system was constructed according to the preferred approach described herein. Measurements have been made with this measurement approach as compared with the prior approach. When only the negative peak voltage $V_{peak-}$ is used to determine the mixture composition, as in the prior approach, there is typically about a 10 percent variation in the determined mixture composition as compared with the actual mixture composition. That is, if the actual mixture composition is 20 percent alcohol, the measured mixture composition may be as low as 18 percent or as high as 22 percent. When the preferred embodiment of the present approach using both $V_{peak-}$ and $V_{peak+}$ is used, the variation is reduced to about 1 percent variation, a significant improvement for the control of the engine.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for measuring the composition of an electrically conductive mixture, comprising
a single sensor including a first electrode and a second electrode with a measurement space therebetween for receiving a specimen of an electrically conductive mixture, the second electrode being connected to a fixed second electrode potential;
a voltage source having as an output an applied voltage;
a voltage oscillator switch which alternatively switches the first electrode between two different circuit elements, the voltage oscillator switch being operable to alternatively connect the first electrode to a reference discharge voltage and to the applied voltage through a resistor, there being a first operational state encompassing the period when the first electrode is connected to the reference discharge voltage and a second operational state encompassing the period when the first electrode is connected to the applied voltage through the resistor;
a first measurement circuit element having an input in electrical communication with the first electrode and an output of a first operational state peak voltage measured during the first operational state;
a second measurement circuit element having an input in electrical communication with the first electrode and an output of a second operational state peak voltage measured during the second operational state; and
a mathematical circuit element having as inputs the first operational state peak voltage and the second operational state peak voltage, and as a voltage output a mathematical function of the first operational state peak voltage and the second operational state peak voltage.

2. The apparatus of claim 1, wherein the applied voltage output of the voltage source is positive relative to the reference discharge voltage, the first operational state peak voltage is negative, and the second operational state peak voltage is positive.

3. The apparatus of claim 1, wherein the sensor is generally cylindrically symmetric and each of the electrodes is cylindrical, one of the electrodes having a smaller cylindrical diameter than the other electrode and being disposed inside and in facing relationship to the other electrode.

4. The apparatus of claim 1, wherein the voltage oscillator switch is a transistor.

5. The apparatus of claim 1, wherein the first measurement circuit element is a comparator/pulse integrator feedback circuit.

6. The apparatus of claim 1, wherein the second measurement circuit element is an operational amplifier/comparator circuit.

7. The apparatus of claim 1, wherein the mathematical circuit element has as an output the sum of the first operational state peak voltage and a preselected constant proper fraction of the second operational state peak voltage.

8. The apparatus of claim 7, wherein the preselected constant proper fraction is from about 0.1 to about 0.2.

9. The apparatus of claim 7, wherein the preselected constant proper fraction is about 0.15.

10. The apparatus of claim 1, wherein the voltage oscillator switch operates at a frequency of from about 5 to about 10 kilohertz.

11. The apparatus of claim 1, further including
a controller which correlates the voltage output to the composition of a mixture.

12. The apparatus of claim 1, wherein the reference discharge voltage is ground.

13. The apparatus of claim 1, wherein the fixed second electrode potential is ground.

14. A method for measuring the composition of an electrically conductive mixture, comprising the steps of
providing a single sensor including a first electrode and a second electrode with a measurement space therebetween, the second electrode being connected to a fixed second electrode potential;
placing a specimen of an electrically conductive mixture in the measurement space;
alternatively connecting the first electrode to ground and to an applied voltage through a resistor, a first operational state encompassing the period when the first electrode is connected to ground and a second operational state encompassing the period when the first electrode is connected to the applied voltage through the resistor;
measuring a first operational state peak voltage during the first operational state;
measuring a second operational state peak voltage during the second operational state; and
mathematically calculating a function of the first operation state peak voltage and the second operational state peak voltage to obtain a voltage output.

15. The method of claim 14, wherein the step of placing includes the step of
providing a mixture of gasoline and alcohol.

16. The method of claim 14, including an additional step, after the step of summing, of
correlating the voltage output with the composition of the mixture.

17. The method of claim 14, wherein the step of alternatively connecting includes the step of
providing an applied voltage that is positive relative to the fixed second electrode potential, and wherein the fixed second electrode potential is ground.

18. The method of claim 14, wherein the step of mathematically combining includes the step of
summing the first operational state peak voltage and a preselected constant proper fraction of the second operational state peak voltage to obtain a summed voltage output.

19. Apparatus for measuring the composition of an electrically conductive mixture, comprising
a single sensor including a first electrode and a second electrode with a measurement space therebetween, the second electrode being connected to a fixed second electrode potential;
a switch having a first pole in electrical communication with the first electrode and an applied voltage through a resistor, and a second pole in electrical communication with a reference discharge voltage, there being a first operational state encompassing the period when the switch is closed so that the first electrode is connected to the reference discharge voltage, and a second operational state encompassing the period when the switch is open so that the first electrode is connected only to the applied voltage through the resistor;
a first measurement circuit element having an input in electrical communication with the first electrode and an output of a first operational state peak voltage measured during the first operational state;
a second measurement circuit element having an input in electrical communication with the first electrode and an output of a second operational state peak voltage measured during the second operational state, wherein the second operational state peak voltage has an opposite sense relative to the first operational state peak voltage; and a mathematical circuit element having as inputs the first operational state peak voltage and the second operational state peak voltage, and as a voltage output a mathematical function of the first operational state peak voltage and the second operational state peak voltage.

20. The apparatus of claim 19, wherein the mathematical circuit element has as an output the sum of the first operational state peak voltage and a preselected constant proper fraction of the second operational state peak voltage.

* * * * *